(12) United States Patent
Louvrier et al.

(10) Patent No.: US 9,930,765 B2
(45) Date of Patent: Mar. 27, 2018

(54) DYNAMIC DAMPER IN AN X-RAY SYSTEM

(71) Applicant: General Electric Company, Schenectady, NY (US)

(72) Inventors: Yannick Louvrier, Buc (FR); Philippe Ernest, Buc (FR); Denis Perrillat-Amede, Buc (FR); Dominique Poincloux, Buc (FR); Christophe Robert, Buc (FR)

(73) Assignee: General Electric Company, Schenectady, NY (US)

(*) Notice: Subject to any disclaimer, the term of this patent is extended or adjusted under 35 U.S.C. 154(b) by 77 days.

(21) Appl. No.: 15/015,920

(22) Filed: Feb. 4, 2016

(65) Prior Publication Data

US 2017/0231076 A1 Aug. 10, 2017

(51) Int. Cl.
*H05G 1/32* (2006.01)
*A61B 6/03* (2006.01)
*A61B 6/04* (2006.01)
*A61B 6/00* (2006.01)
*H01J 35/06* (2006.01)
*H01J 35/08* (2006.01)
*H05G 1/10* (2006.01)
(Continued)

(52) U.S. Cl.
CPC ............... *H05G 1/32* (2013.01); *A61B 6/032* (2013.01); *A61B 6/0407* (2013.01); *A61B 6/40* (2013.01); *A61B 6/5211* (2013.01); *H01J 35/06* (2013.01); *H01J 35/08* (2013.01); *H05G 1/10* (2013.01); *H05G 1/54* (2013.01); *H05G 1/58* (2013.01)

(58) Field of Classification Search
CPC ... A61B 6/00; H05G 1/00; H05G 1/02; H05G 1/08; H05G 1/10; H05G 1/12; H05G 1/14; H05G 1/16; H05G 1/20; H05G 1/30; H05G 1/32; H05G 1/48; H05G 1/58; H01J 35/22; H01J 35/025
USPC .................. 378/91, 101, 103, 105, 111, 112
See application file for complete search history.

(56) References Cited

U.S. PATENT DOCUMENTS

| 5,661,774 A | 8/1997 | Gordon et al. |
| 7,114,850 B2 | 10/2006 | Dong et al. |
| 7,529,344 B2 | 5/2009 | Oreper |

(Continued)

FOREIGN PATENT DOCUMENTS

| CN | 101754561 A | 6/2010 |
| EP | 0497517 A1 | 8/1992 |
| EP | 0933980 A2 | 8/1999 |

OTHER PUBLICATIONS

Partial European Search Report issued in connection with corresponding EP Application No. 17153809.3 dated Jul. 7, 2017, 11 pages.

*Primary Examiner* — Jurie Yun
(74) *Attorney, Agent, or Firm* — Andrus Intellectual Property Law, LLP

(57) ABSTRACT

In an X-ray generator an X-ray tube includes an anode and a cathode and is energized with at least a first high voltage potential. A dynamic damper with a frequency dependent impedance is interposed between the X-ray tube and a source of the high voltage potential. The impedance of the dynamic damper increases with an increase in frequency associated with tube-spit. In an X-ray generator with resonant switching to provide a first kV level and a second kV level to the X-ray tube, the impedance of the dynamic damper is low at the operational frequency of the resonant switch to promote energy recovery when the resonant switch operates to provide a first kV level to the X-ray tube.

20 Claims, 4 Drawing Sheets

(51) Int. Cl.
*H05G 1/54* (2006.01)
*H05G 1/58* (2006.01)

(56) References Cited

U.S. PATENT DOCUMENTS

| | | |
|---|---|---|
| 7,620,151 B2 | 11/2009 | Sundaram et al. |
| 7,792,241 B2 | 9/2010 | Wu et al. |
| 8,165,264 B2 | 4/2012 | Zou |
| 2012/0155613 A1 | 6/2012 | Caiafa et al. |
| 2012/0155614 A1 | 6/2012 | Caiafa et al. |
| 2015/0207415 A1 | 7/2015 | Caiafa et al. |

DYNAMIC DAMPER IN AN X-RAY SYSTEM

BACKGROUND

The present disclosure is related to the field of X-ray imaging. More specifically, the present disclosure relates to dynamic damping of high voltage input power to an X-ray source.

In conventional computed tomography (CT) X-ray imaging systems, an X-ray source emits a cone-shaped X-ray beam toward a subject or object, such as a patient or piece of luggage. The beam, after being attenuated by the subject, impinges upon an array of radiation detectors. The intensity of the attenuated beam radiation received at the detector array is dependent upon the attenuation of the X-ray beam by the subject. Each detector element of the detector array produces a separate electrical signal indicative of the X-ray intensity received by that particular detector element. The electrical signals are quantized and transmitted to a data processing system for analysis, which generally results in the presentation of an image.

CT imaging systems may comprise energy-discriminating (ED), multi-energy (ME), and/or dual-energy (DE) CT imaging systems that may be referred to as an EDCT, MECT, and/or DECT imaging system. The EDCT, MECT, and/or DECT imaging systems are configured to measure energy-sensitive projection data. The energy-sensitive projection data may be acquired using multiple applied X-ray spectra by modifying the operating voltage of the X-ray tube or utilizing X-ray beam filtering techniques (e.g., energy-sensitive X-ray generation techniques), or by energy-sensitive data acquisition by the detector using energy-discriminating, or with photon counting detectors or dual-layered detectors (e.g., energy-sensitive X-ray detection techniques).

With X-ray generation techniques, various system configurations utilize modification of the operating voltage of the X-ray tube including: (1) acquisition of projection data from two sequential scans of the object using different operating voltages of the X-ray tube, (2) acquisition of projection data utilizing rapid switching of the operating voltage of the X-ray tube to acquire low-energy and high-energy information for an alternating subset of projection views, or (3) concurrent acquisition of energy-sensitive information using multiple imaging systems with different operating voltages of the X-ray tube.

EDCT/MECT/DECT provides energy discrimination capability that allows material characterization. For example, in the absence of object scatter, the system utilizes signals from two applied photon spectra, namely the low-energy and the high-energy incident X-ray spectrum. The low-energy and high-energy incident X-ray spectra are typically characterized by the mean energies of the applied X-ray beams. For example, the low-energy X-ray spectrum comprises X-ray photons with lower-energy photons, resulting in a lower mean energy, relative to the high-energy X-ray spectrum. The detected signals from low-energy and high-energy X-ray spectra, either from two different applied spectra (X-ray generation techniques) or by regions of the same applied spectrum (X-ray detection techniques) provide sufficient information to estimate the effective atomic number of the material being imaged. Typically, X-ray attenuation mechanisms (Compton scattering or Photoelectric absorption) or the energy-sensitive attenuation properties of two basis materials (typically water and calcium for patient scanning) are used to enable estimation of the effective atomic number.

Dual-energy scanning can obtain diagnostic CT images that enhance contrast separation within the image by utilizing energy-sensitive measurements. To facilitate processing of the energy-sensitive measurements, the applied X-ray spectrum should be constant during an integration period. For example, such CT systems that acquire interleaved subsets of low-energy and high-energy projection data (versus two separate scans) should operate to maintain the accelerating voltage steady during an acquisition interval. Also, the change from one voltage level to another voltage level should occur very rapidly. Less stable X-ray tube operating voltages and/or slower operating voltage switching times result in a reduction in the difference in effective mean energy (the average of the mean energy of time-varying X-ray spectrum) of the applied X-ray spectra, which reduces the fidelity of the system in characterizing different materials.

The term "tube-spit" refers to temporary electrical short-circuits that sometimes occur inside an x-ray tube. Typically, upon the occurrence of tube-spit, the supply of power to the x-ray tube is temporarily interrupted to prevent arcing. Power is restored to the tube after a time interval of, for example, about one millisecond. During tube-spit recovery, no x-ray photon is emitted from the x-ray tube. As a result, detector measurements taken during the recovery are invalid.

BRIEF DISCLOSURE

An exemplary embodiment of an X-ray generator includes an X-ray tube with an anode and a cathode. A high voltage generator is operable to provide at least a first kV level to the X-ray tube and a second kV level to the X-ray tube. The second kV level is higher than the first kV level. A dynamic damper has a frequency dependent impedance. The dynamic damper is interposed between the cathode of the X-ray tube and the high voltage generator. The impedance of the dynamic damper increases with an increase in frequency.

An exemplary embodiment of a method of protecting against tube spit in an X-ray generator includes supplying an X-ray tube with a high voltage potential from a high voltage tank assembly with a transformer. A dynamic damper is interposed between a cathode of the X-ray tube and the transformer. The dynamic damper provides a frequency variable impedance. While the X-ray tube is supplied with the high voltage potential, a first impedance of the dynamic damper is provided. Upon occurrence of tube spit within the X-ray tube, a second impedance of the dynamic damper is provided. The second impedance is greater than the first impedance.

An exemplary embodiment of a high voltage tank assembly in an X-ray generator includes a transformer assembly. The transformer assembly receives high frequency input power. A voltage rectifier is coupled to the transformer assembly. The voltage rectifier receives an input voltage from the transformer assembly and provides an output voltage at a first kV level. The transformer assembly and voltage rectifier are operable to selectively provide the first kV level to the X-ray tube and to provide a second kV level to the X-ray tube. The second kV level is higher than the first kV level. A dynamic damper has a frequency dependent impedance. The Dynamic damper is interposed between the X-ray tube and the voltage rectifier. The impedance of the dynamic damper increases with an increase in frequency.

DETAILED DISCLOSURE

Figure 3:
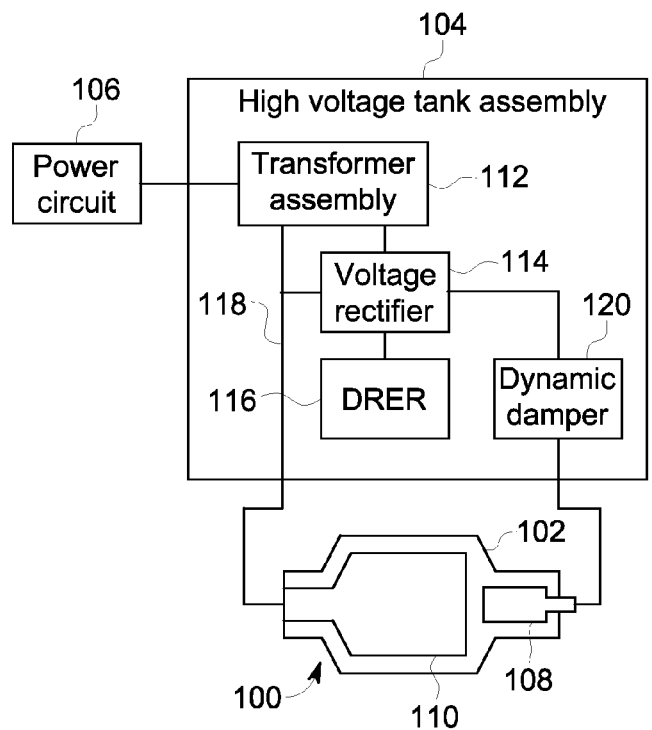
FIG. 3 is a system diagram of an exemplary embodiment of an X-ray generator.

FIG. 3 is a system diagram of an exemplary embodiment of an X-ray generator 100. It will be understood that the schematic diagram of FIG. 4 and the circuit diagram of FIG. 5 represent more detailed, but merely exemplary embodiments of the radiation generator 100. Other implementations of the radiation generator 100 may be recognized by a person of ordinary skill in the art in view of the Figures and description provided herein. In the embodiment depicted in FIG. 3 and as described in detail herein, the X-ray generator 100 includes a high voltage source and a radiation source which is exemplarily an X-ray tube 102 electrically coupled in a conventional manner to a high voltage tank assembly 104 so as to create an emission of X-rays from the X-ray tube 102. A person of ordinary skill in the art will understand that while the high voltage tank assembly 104 is depicted as including various components located therein, alternative embodiments may include more or fewer components located within the high voltage tank assembly 104 in an arrangement additional to that as depicted herein. The radiation generator 100 further includes a power circuit 106 which is coupled to the high voltage tank assembly 104 and configured to supply power to drive the high voltage tank assembly 104.

The X-ray tube 102 generally includes a cathode 108 and an anode 110. The cathode 108 and anode 110 are arranged in a generally opposing alignment along a longitudinal axis of the X-ray tube 102. The cathode 108 includes an electron-emitting filament that is capable in a conventional manner of emitting electrons. A filament heating current controls the number of electrons boiled off by the filament and thus provides control of the tube current flow. The high voltage potential applied by the high voltage tank assembly 104 causes acceleration of the electrons from the cathode 108 towards the anode 110. The accelerated electrons collide with the anode 110, producing electromagnetic radiation, including X-radiation.

The high voltage tank assembly 104 is configured to receive an AC waveform from the power circuit 106 and condition the AC wave form to provide a high voltage DC potential to the X-ray tube where the anode 110 and the cathode 108 usually carry equal voltages of different polarity. The high voltage tank assembly 104 includes a transformer assembly 112 and a voltage rectifier circuit 114. The transformer assembly 112 and the voltage rectifier circuit 114 of the high voltage tank assembly 110 condition the AC voltage signal transferred by the power circuit 106.

The voltage rectifier 114 is connected to a distributed resonant energy recovery (DRER) circuit 116. The DRER circuit 116, as described in further detail herein can store and restore energy to the X-ray tube 102 between a high kV level (e.g. 140 kV) and a low kV level (e.g. 80 kV) the DRER circuit 116 further promotes efficiency by reusing and recirculating energy when switching between the voltage levels which conserves energy and allows faster switching.

The transformer assembly 112 and voltage rectifier 114 provide the high voltage energy to the X-ray tube necessary to generate X-rays. This high voltage energy can be between two or more output energy levels. In one example the energy can be switched between zero and 120 kV, while in another embodiment, the energy can be switched between 80 kV and 140 kV. A person of ordinary skill in the art will recognize other energy levels or combinations of two or more energy levels that may be used in embodiments.

As discussed above, temporary electrical short circuits sometimes occur inside of an X-ray tube which are generally referred to as tube-spit. During tube-spit recovery no X-ray photon is emitted from the X-ray tube. As disclosed herein, a dynamic damper 120 is provided between the cathode 108 of the X-ray tube 102 and the voltage rectifier 114. The dynamic damper 120 provides an impedance against the short circuit of the tube-spit to limit the value of the in rush current and protect components. As described in further detail herein, the dynamic damper 120 has a frequency variable impedance to provide a high impedance in response to the high frequency characteristic of tube-spit while providing a low impedance during the normal operation, including normal X-ray generator operational frequencies and working frequencies of the energy storage system.

In an optional and exemplary embodiment, the X-ray generator 100 may further include a distributed resonant energy recovery (DRER) circuit 116 connected to the voltage rectifier 114. An energy recovery system, for example, the DRER circuit 116, as described in further detail herein can help to provide the switching of the energy between two or more energy levels by speeding up the transition between the energy levels by storing and returning energy. In embodiments, this may be provided as resonant switching of the voltage generated by the transformer and voltage rectifier to the X-ray tube 102 between a high kV level (e.g. 140 kV) and a low kV level (e.g. 80 kV). The DRER circuit 116, as described in further detail herein may operate to switch the load on an output capacitor to transfer energy from the output capacitor to a storage capacitor to recover energy from the system when switching between energy levels.

Figure 1:
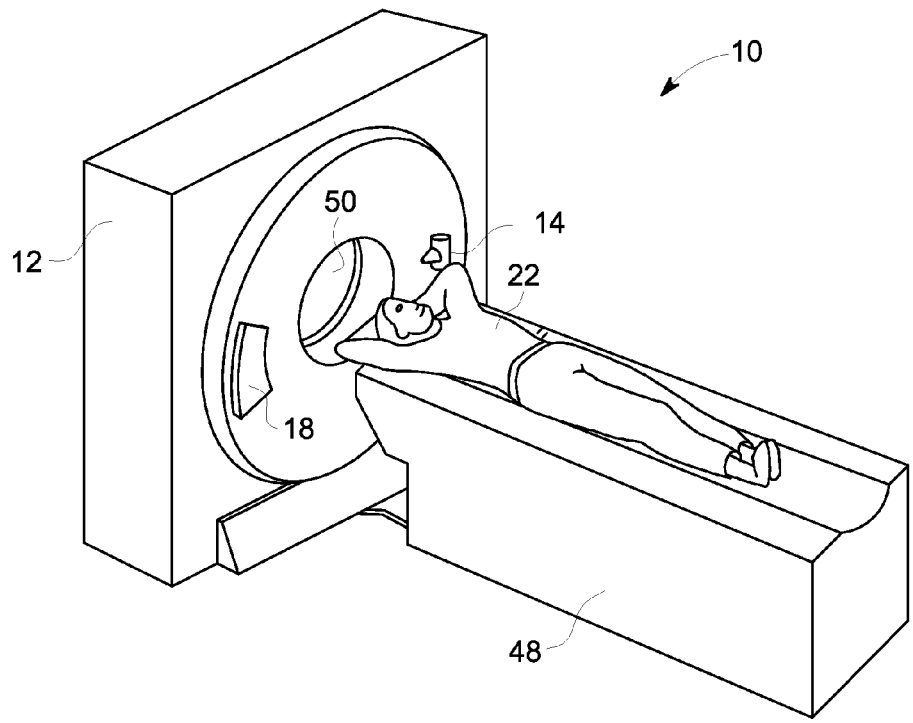
FIG. 1 depicts a computed tomography (CT) imaging system in connection with which various embodiments may be implemented.
Figure 2:
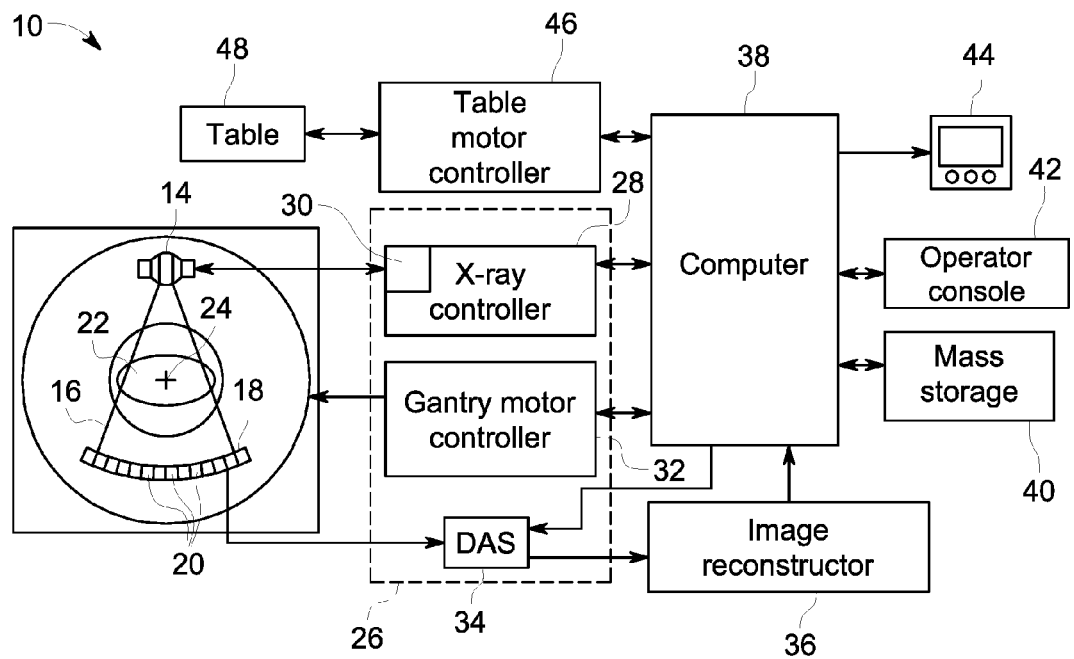
FIG. 2 is a block schematic diagram of the CT imaging system of FIG. 1.

FIG. 1 is a pictorial view of a CT imaging system 10. FIG. 2 is a schematic diagram of the CT imaging system 10. In the exemplary embodiment, the CT imaging system 10 is shown as including a gantry 12 representative of a "third generation" CT imaging system. The gantry 12 has an X-ray source 14 that projects a cone beam 16 of X-rays towards a detector array 18 on the opposite side of the gantry 12. The detector array 18 may be formed by a plurality of detector rows (not shown) including a plurality of detector elements 20 that together sense the projected X-ray beams that pass through an object, such as a medical patient 22, a piece of luggage, or an industrial object dependent upon the application of the imaging device. Each detector element 20 may produce an electrical signal that represents the intensity of an impinging X-ray radiation beam and hence is indicative of the attenuation of the beam as it passes through the object (e.g. patient 22). The intensity may correspond to the number of incident photons at the element. An imaging system 10 having a multi slice detector 18 may be capable of providing a plurality of images representative of a volume of the object 22. Each image of the plurality of images corresponds to a separate "slice" of the volume. The "thickness" or aperture of the slice is dependent on the height of the detector rows.

During a scan to acquire X-ray projection data, a rotating section within the gantry 12 and the components mounted thereon rotate above a center of rotation 24. FIG. 2 shows only a single row of detector elements 20. However, the multi slice detector array 18 may include a plurality of parallel detector rows of detector elements 20 such that projection data corresponding to the exemplary cone-beam geometry could be acquired simultaneously during a scan. It will be recognized that other imaging systems may use different beam geometry and the detector 18 may be similarly adapted to detect the X-rays of the emitter geometry. Rotation of components within the gantry 12 and the operation of the radiation source 14 may be covered by a control apparatus 26. The control apparatus 26 includes an X-ray controller and generator 30 that provide power and timing signals to the X-ray source 14. A gantry motor controller 32 controls the rotational speed and position of the rotating portion of the gantry 12. A data acquisition system (DAS) 34 in the control apparatus 26 sample analog data from the detector elements 20 and converts the data to digital signals for subsequent processing. An image reconstructor 36 receives sampled and digitized measurement data from the DAS 34 and performs high-speed image reconstruction. The reconstructed image is applied as an input to a computer 38 that stores the image in a mass storage device 40. Although shown as a separate device in FIG. 2, in additional embodiments, the image reconstructor 36 may be special hardware located inside the computer 38 or software stored on a computer readable medium 52 in the computer 38 or accessible by the computer 38 and executed by the computer 38. The computer readable medium may be integrated, removable, or communicatively connected memory capable of being read by a reading device of the computer 38. The computer 38 may execute instructions stored in firmware or software on the removable medium 52.

The computer 38 also receives commands and scanning parameters from an operator via a console 42 that has a key board and/or another form of user input device. An associated display system 44 allows the operator to observe the reconstructed image and other data from the computer 38. The operator supplied commands and parameters may be used by the computer 38 to provide control signals and information to the DAS 34, X-ray controller 28. Generator 390 and gantry motor controller 32. In addition, the computer 38 operates a table motor controller 46 that controls a motorized table 48 to position the patient 22 in the gantry 12. The table 48 moves portions of the patient 22 through a gantry opening 50.

Figure 4:
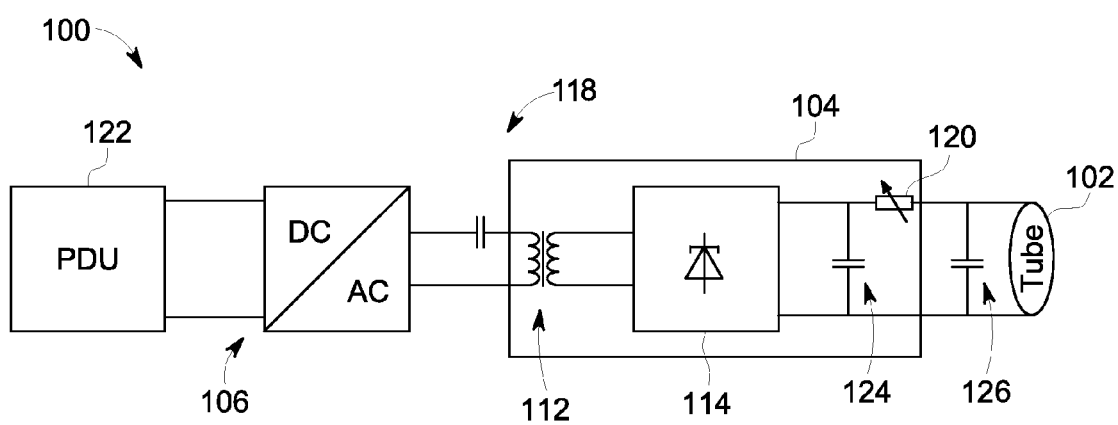
FIG. 4 is a schematic diagram of an exemplary embodiment of an X-ray generator with spit damping.
Figure 5:
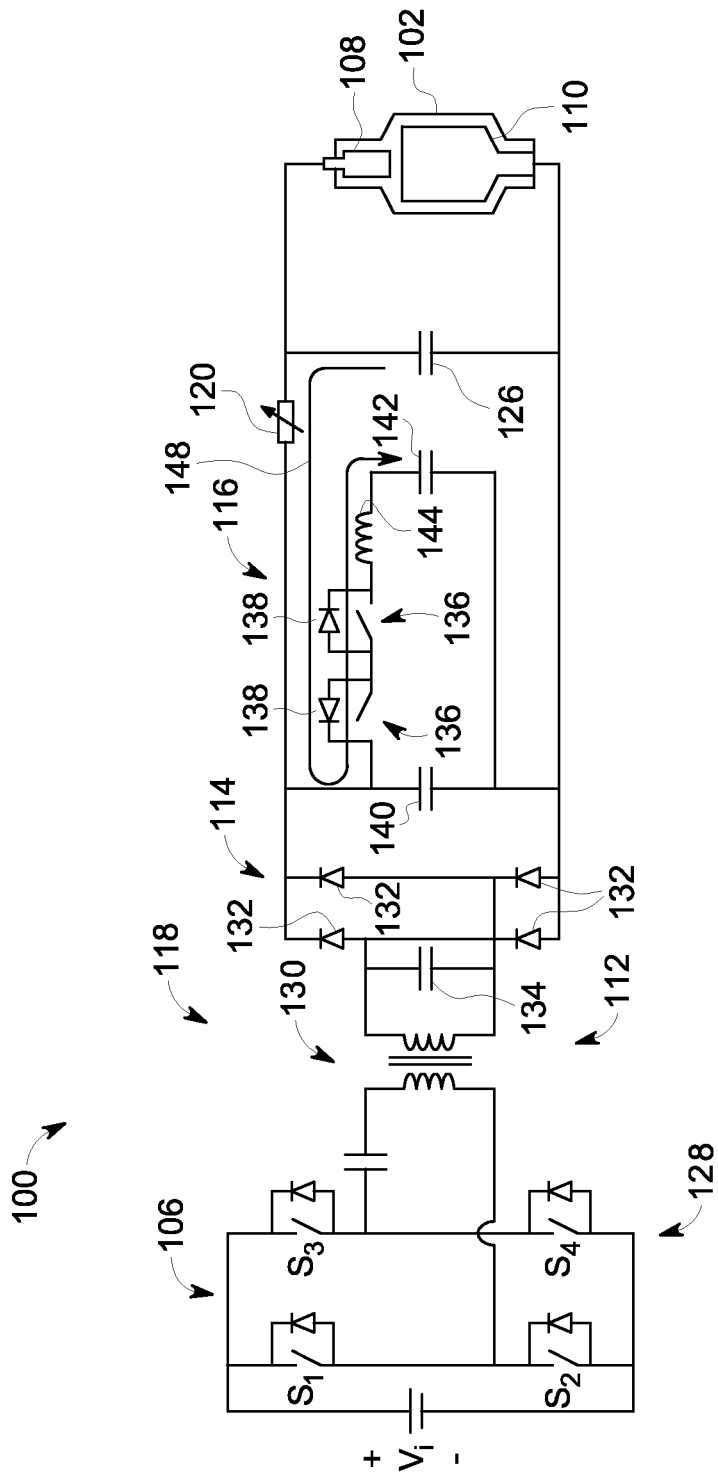
FIG. 5 is a circuit diagram of an exemplary embodiment of an X-ray generator with an energy storage system and spit damping.

FIG. 4 is a schematic diagram of an exemplary embodiment of the X-ray generator 100 with tube-spit damping. The X-ray generator 100 includes a power circuit 106 that receives electrical main power from a power distribution unit (PDU) 122. The PDU 122 provides the external input power to the power circuit 106. In a merely exemplary embodiment, the PDU 122 provides power at an exemplary 50 Hz input frequency. The power circuit 106 exemplary includes a frequency converter which produces a high frequency input power signal to the transformer assembly 112. The high frequency input power signal may exemplarily have a frequency between 50 kHz to 250 kHz. The high frequency input power signal includes an AC component and a DC component to provide both the input voltage for the high voltage tank assembly 104 to develop the high voltage potentials necessary to generate the X-rays as. The power from the power circuit is provided into the high voltage tank assembly 104 and the transformer assembly 112 located therein.

As described above, the transformer 112 and voltage rectifier 114 generate the high voltage potentials required by the X-ray tube to generate X-rays. Particularly, in dual energy (DE) or multiple energy (ME) X-ray applications, the transformer 112 and voltage rectifier 114 are capable of generating multiple voltage levels across the X-ray tube 102. In exemplary embodiments, one or more of the frequency converter, transformer assembly 112, and voltage rectifier 114 comprise a high voltage generator 118 of the X-ray generator 110. A filtering capacitor 124 is provided in parallel to the voltage rectifier 114. An output capacitor 126 is arranged in parallel to the X-ray tube 102 and controls the voltage applied across the X-ray tube 102 and stores potential for recapture and reuse. In embodiments, the capacitance of the output capacitor 126 may at least partly comprised of the capacitance of a high voltage cable linking the high voltage generator and the X-ray tube. The capacitance of the output capacitor may be greater than that of the filtering capacitor 124.

As explained in further detail herein, a dynamic damper 120 is located between the X-ray tube 102 and the voltage rectifier 114. As explained above, tube-spit is a high frequency phenomenon of short circuits within the X-ray tube 102. Tube-spit can occur at a frequency about 10 MHz, although typically tube-spit has a fundamental frequency higher than 20 MHz. A high impedance provided by dynamic damper 120 at these frequencies protects the system against the occurrence of tube-spit. However, a high damping impedance reduces the efficiency of energy recovery. Therefore, a dynamic damper 120 which produces a frequency-variable impedance can provide a low impedance at low frequencies associated with operation of the X-ray generator 100, including embodiments with energy storage systems as described herein while providing a high impedance when high frequency tube-spit phenomenon occur. This arrangement achieves both improved tube-spit protection, as well as improved energy recovery, particularly in systems that use resonant switching.

FIG. 5 is a circuit diagram of an exemplary embodiment of the X-ray generator 100 with an energy recovery system and tube-spit damping. The circuit diagram of FIG. 5 exemplarily provides one possible embodiment of an implementation of the device as described above with respect to FIGS. 3 and 4. Particularly, FIG. 5 depicts one embodiment that uses a DRER circuit. It will be recognized by a person of ordinary skill in the art that other implementations and embodiments may be used while remaining within the scope of the present disclosure.

Exemplarily, the power circuit 106 includes a frequency converter 128 which is operable to provide the desired voltage and current to the X-ray tube. Exemplarily, the frequency converter 128 is arranged as a full HV inverter. However, it will be recognized that in alternative embodiments, the frequency converter 128 may be arranged and operated in other manners, including more than two channels.

The power frequency converter 128 provides the energization through the transformer assembly 112 which in embodiments may include a plurality of transformers. While not depicted, the transformer assembly 112 may exemplarily include an HV tank transformer although persons of ordinary skill in the art will recognize other transformer arrangements as well. One or more of these transformers of the transformer assembly 112 may be located within the high voltage tank assembly (not depicted).

In exemplary embodiments, a resonant capacitor 134 may be connected in parallel to the transformers of the transformer assembly 112, including, but not limited to the HV tank transfer 128. It will be noted that in dual energy (DE) embodiments, the power supply is on and provides the necessary power to keep the high HV level constant. The power supply is exemplarily turned off before the transmission from the high kV to a low kV.

The power provided from the transformer assembly 112 is provided to a voltage rectifier 114. The voltage rectifier 114 exemplarily includes diodes 132. The diodes may exemplarily be arranged as a full bridge rectifier as depicted in FIG. 5. In another embodiment, the voltage rectifier 114 may include capacitors (not depicted) and instead be arranged as a voltage doubler rectifier. As described above, a high voltage generator 118 of the X-ray generator 100 may comprise one or more of the frequency converter 128, transformer assembly 112, and the voltage rectifier 114. In embodiments, the transformer assembly 112 and the voltage rectifier 114 may be located within the high voltage (HV) tank.

As described above, the energy recovery system exemplified by the DRER circuit 116 provides an ability to store energy to facilitate switching of the voltage generated by the system between a high kV level and a low kV level. The DRER circuit 116 in the implementation as described herein further facilitates the recovery and reuse of energy when switching between the voltage levels which conserves the energy and allows faster switching. The DRER circuit 116 depicted in FIG. 5 is exemplarily arranged in an active resonant configuration which the electronics in the system can transmit power to the X-ray tube 102, for example to charge to continue to provide power to the X-ray tube 102 at high voltage operation. For example, the radiation generator 100 may operate to provide energy from the voltage rectifier 114 at 80 kV and energy may be provided to the X-ray tube 102 at 140 kV by combining operation of both the voltage rectifier 114 and the DRER circuit 116. The exemplary embodiment of the DRER circuit 116 depicted in FIG. 5 includes a plurality of switching devices 136 connected in series. The switching devices 136 may be any type of switches. For example, the switching devices 136 may be metal-oxide semiconductor field-effect transistors (MOSFETS), insulated gate bi-polar transistors (IGBTS), thyristors, BJT, or any other device with a controllable on feature. Such devices may be made of silicon, silicon-carbide, gallium nitride, or any other material suitable for building such controllable devices. While not depicted in FIG. 5, it is understood that the switching devices 136 are connected to a control circuit, which may include a control driver which may exemplarily be a logic clock and may further include inverting buffers such that the switching devices 136 are operated in opposite states with respect to one another. In still further embodiments, depending upon the operation of the radiation generator (e.g. conventional v. dual energy operation), the switching devices may be operable to be in the same state simultaneously.

The switching devices 136 are connected between a system capacitor 140 and a DRER capacitor 142. The diodes can be made of any suitable materials such as, but not limited to, silicon, silicon carbide, gallium nitrate, etc. Each of the switching devices, 136 is connected in an anti-parallel configuration with diodes 138, which operate as opposing blocking diodes. The DRER inductor 144 is also connected in series between the DRER capacitor 142 and the switches 136/diodes 138. It should be noted that the DRER inductor 144 may also be referred to as a resonance inductor. In some embodiments there may be more than one system capacitor 140 (e.g. arranged in series) and/or more than one DRER capacitor 142 (e.g. arranged in series), as well as multiple DRER inductors 144 (e.g. arranged in series), as will be recognized by one of ordinary skill in the art.

As described above, a dynamic damper 120 may exemplarily be a solenoid that is positioned between the anode 110 of the X-ray tube 102 and the DRER circuit 116. The solenoid may exemplarily be a winding of wire around magnetic stainless steel. In exemplary embodiments, the shape and dimensions of the solenoid will depend upon the geometric constrains within the HV tank and the desired resistance value at low frequencies which is the predominant condition that the solenoid will experience for normal operating condition.

Figure 6:
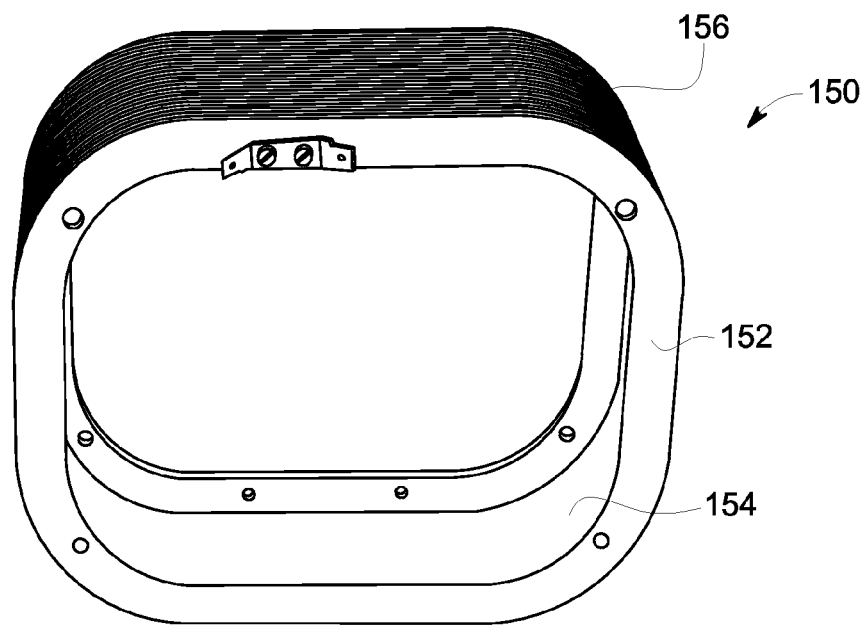
FIG. 6 depicts an exemplary embodiment of a dynamic damper.

FIG. 6 depicts an exemplary embodiment of a solenoid 150. Exemplarily, the solenoid 150 is constructed with magnetic stainless steel wire 156 wound around a frame 154. The frame 154, which may include sides 152, may be constructed of plastic or polycarbonate, or other suitable material as will be recognized by a person of ordinary skill in the art. While the solenoid 150 is depicted as being a generally square shape, it will be recognized that in view of this disclosure, the solenoid 150 may take on any number of geometric shapes and sizes, for example due to desired impedance at low frequencies. The size and shape is selected for the desired impedance, for example the length of the stainless steel wire is determinative of the resistance of the solenoid and the size and shape of the windings are determinative of the inductance. Together, these are selected for the desired impedance characteristics within physical HV tank size constraints.

In embodiments, the impedance increase at high frequencies provided by the dynamic damper may be a result of the inductance of the solenoid. Additionally, further impedance increase may be provided by frequency dependent increase in the resistance of the stainless steel wire. This increased resistance can be important to mitigate or damp the resonance between the inductance of the solenoid and the capacitances of the capacitors 140 and 146. Skin effect increases the resistance of the wire with increases in frequency. The corner frequency of the skin effect, where the resistance starts increasing, is determined from a combination of wire diameter, material conductance, and material magnetic permeability. Stainless steel wire provides a combination of these properties to achieve a corner frequency just above the frequency of normal operation (e.g. 50 kHz). Therefore, stainless steel wire is particularly useful in embodiments compared to copper wire or other materials generally used for wire wound resistors.

Figure 7:
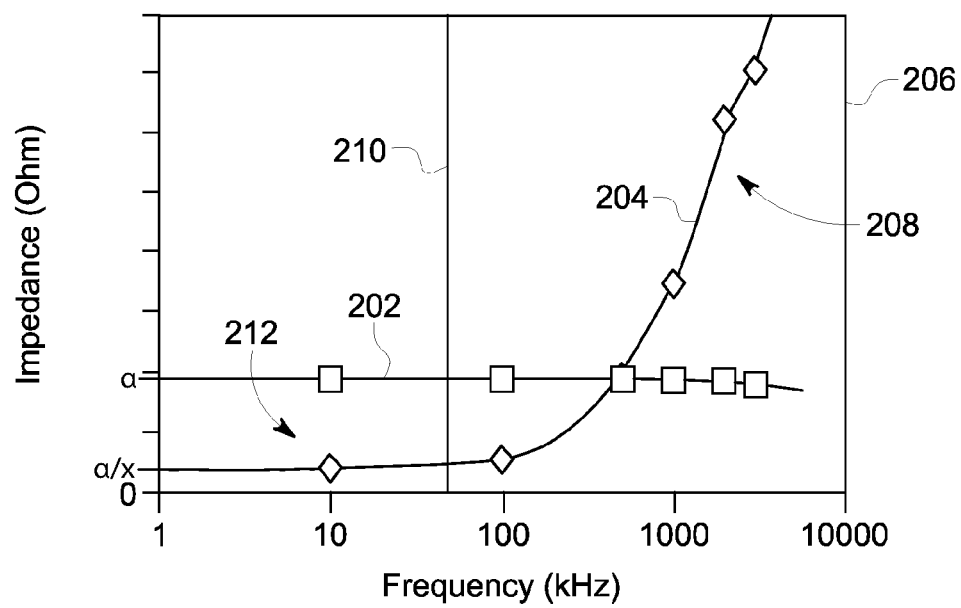
FIG. 7 is a graph of exemplary measurements of impedance versus frequency of an exemplary embodiment of the dynamic damper.

FIG. 7 is a graph 200 that depicts exemplary graph of impedance (e.g. Ohms) versus frequency (kHz) for a measured impedance 202 from an exemplary fixed value resistor compared to the measured impedance 204 across a dynamic damper as disclosed herein. As depicted in FIG. 7, the impedance of an exemplary fixed value resistor is represented as $\alpha$. In embodiments $\alpha$ may represent an impedance needed to protect the high voltage generator, and particularly the voltage rectifier from damage in the even of tube spit. In exemplary embodiments, $\alpha$ may exemplarily range between 500Ω and 15,000Ω. In embodiments where spit protection is provided by a fixed value resistor, $\alpha$ may be understood to exemplarily range between 500Ω and 5,000Ω. Persons of ordinary skill in the art will recognize that such fixed value resistor values may be selected based upon the energy level(s) of the X-ray generator and/or other system considerations. As previously highlighted, the dynamic damper provides two functions. First, the dynamic damper provides a high impedance at high frequencies to provide protection against tube-spit which is greater than 10,000 kHz, represented at 206. This function can be seen in the exponential increase in impedance at 208 as the frequency approaches 5,000 kHz, and more particularly 10,000 kHz. Secondly, the dynamic damper provides minimal impedance at low frequencies, particularly those frequencies experienced during the normal operation of the CT device. This operational frequency is typically between 0 and 100 kHz, and more particularly between 0 and 50 kHz. In additional embodiments the operation frequency may be between 20 kHz and 200 kHz.

FIG. 7 shows that the impedance of the dynamic damper 204 ranges from $\alpha/x$ at low frequencies to greater than $\alpha$ at frequencies greater than 5,000 kHz, and further at frequencies approaching 10,000 kHz. Exemplarily "x" may be 3 or 4 and therefore the dynamic damper provides a frequency variable impedance exemplarily between at least $3^{-1}\alpha$ or $4^{-1}\alpha$ to greater than $\alpha$. It will be understood other values of "x" may also be used in embodiments and that these values represent minimum ranges and in practice the impedance may exceed these values. In embodiments, the impedance may increase to e.g. $3\alpha$ or $4\alpha$ at frequencies greater than 5 MHz or 10 MHz. in still further embodiments, the low impedance value of the dynamic damper may be less than $4^{-1}\alpha$ at frequencies less than 50 kHz, including, but not limited to $10^{-1}\alpha$. For example, a embodiment of a radiation generator with resonant switching and a seven microsecond transition time between the high and low energy levels may produce a resonant frequency of about 50 kHz as indicated at line 210. Therefore, at these low frequency levels communicated by the arrow 212 the dynamic damper exhibits low impendence, exemplarily $\alpha/3$ or $\alpha/4$ Ohms. In practice, this may result in a low impedance value of 500 Ohms or less at frequencies less than 50 kHz.

The reduced impedance of the dynamic damper at low frequencies, such as less than 100 kHz, and particularly at frequencies less than 50 kHz, is a further improvement over the fixed value resistor. As seen in FIG. 7, the dynamic damper provides a significantly lower impedance at CT operational frequencies. This reduced impedance at CT operational frequencies results in more efficient recovery of energy by the DRER circuit as the system experiences less impedance. This efficiency gain is of particular importance for future applications as the overall efficiencies of the CT system improves and the operational current (mA) increases in CT systems.

Referring back to FIG. 5, during operation, energy is resonantly transferred in the DRER circuit 116 between energy storage elements e.g. system capacitor 140 and output capacitor 126 and DRER capacitor 142. In embodiments, the output capacitor 126 is much larger than the system capacitor 140, therefore more of the energy flow to the DRER capacitor 142 is directed through the dynamic damper 120. The switching speed of the transition between the voltage levels is controlled by the DRER inductor 144. The DRER inductor 144, the DRER capacitor 142, and the system capacitor 140 operate as resonant elements. In some embodiments the value of the system capacitor 140 and the DRER capacitor 142 are set by the geometrical size of, for example, the connecting cable and the X-ray tube; accordingly, the switching speed from one voltage level to another is determined by the value of the DRER inductor 144. For example, the smaller the value of the DRER inductor 144, the faster the transition of the switching speed between high to low voltage levels, and low to high voltage levels. Exemplarily, the transition speed of the switching devices 136 in various embodiments is much faster than the voltage transition speed.

In operation, the DRER capacitor 142 operates to receive energy from the discharging system capacitor 140 and keep or store the energy while the system is operated in the low voltage state, such that the energy may be later used in the transition from the low voltage state to the high voltage state to recharge the system capacitor 140 using the switching operation of the switching devices 136. Thus, through the resonant cycle, the energy stored in the DRER capacitor 142 is transferred back to the system capacitor 140 when the system is in the high voltage state. The system capacitor 140 is maintained at a desired or required voltage by the voltage rectifier 114. The dynamic damper 120 provides the tube-spit protection in a manner that promotes efficiency and recovery of energy through the output capacitor 126 of the HV cable and the X-ray tube 102 back into the HV tank by offering a low impedance to this energy transfer. Exemplarily the energy is transferred through the circuit to the DRER capacitor 142 along line 148.

Testing conducted by the inventors between the dynamic damper as described herein and a fixed impedance found reduced peak to peak current in the dynamic damper set up under the same high frequency high voltage conditions. The inventors also found that at low frequency and low energy a reduction in peak to peak current was found. The results of both of these tests show that under the operating conditions of normal DE or ME radiation generator, the dynamic damper configuration as disclosed herein provides greater energy recovery and efficiency.

The inventors have also observed that the dynamic damper improves the efficiency of the DRER circuit providing improved independence between the voltage transition time and the current in the tube with further respect to the gantry rotation speed. In exemplary embodiments, the DRER circuit with the dynamic damping provides a consistent low kV energy (70 kV) across a range of input currents (e.g. 30 ma-1,000+ ma) and consistent low kV energy across a range of gantry rotation speeds (e.g. 1.0 s/rev-2.0 s/rev).

Therefore, embodiments of the dynamic damper as disclosed herein both protect against tube-spit while improving the efficiency of energy transfer between the tube and HV cable to the HV tank. By providing a damper with a low impedance at a low frequency, the presently disclosed system increases energy round trip efficiency for energy stored in the HV tank.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. An X-ray generator comprising:
a high voltage generator operable to provide an output voltage to an X-ray tube; and a dynamic damper with a frequency dependent impedance in communication with a cathode of the X-ray tube and the high voltage generator.

2. The X-ray generator of claim 1, wherein the dynamic damper is a solenoid.

3. The X-ray generator of claim 2, wherein the solenoid is constructed of magnetic stainless steel wire windings.

4. The X-ray generator of claim 3, wherein the impedance of the dynamic damper comprises an inductance of the solenoid that increases with frequency and a resistance of the magnetic stainless steel wire windings that increases with frequency.

5. The X-ray generator of claim 1, wherein at a frequency less than 50 kHz the dynamic damper provides an impedance less than 1/3 of a reference impedance needed to protect the high voltage generator.

6. The X-ray generator of claim 5 wherein at the frequency less than 50 kHz, the dynamic damper provides an impedance less than 1/10 of the reference impedance needed to protect the high voltage generator.

7. The X-ray generator of claim 5, wherein at frequencies above 5 MHz the dynamic damper provides an impedance greater than the reference impedance needed to protect the high voltage generator.

8. The X-ray generator of claim 5, wherein the reference impedance is between 500 Ohms and 15,000 Ohms.

9. The X-ray generator of claim 1, further comprising a distributed resonant energy recovery (DRER) circuit comprising:
 at least one capacitor; and
 a plurality of switches arranged in series to the at least one capacitor, the switches operable to selectively store energy in the at least one capacitor,
 wherein the high voltage generator is operable to provide output voltages to the X-ray tube at a first kV level and at a second kV level, the second kV level higher than the first kV level, and when the high voltage generator provides an output voltage to the X-ray tube at the first kV level, the energy is received and stored in the at least one capacitor, and when the high voltage generator provides an output voltage to the X-ray tube at the second kV level, energy is discharged from the at least one capacitor to achieve the second kV level.

10. The X-ray generator of claim 9, further comprising:
 a high voltage cable arranged between the high voltage generator and the X-ray tube
 wherein when the high voltage generator is operated to provide the second kV level to the X-ray tube, energy is stored in a capacitance of the high voltage cable, and when the high voltage generator is operated to provide the first kV level to the X-ray tube, the high voltage cable is discharged through the dynamic damper to the DRER circuit to store energy in the at least one capacitor of the DRER circuit.

11. The X-ray generator of claim 1, further comprising:
 a high voltage tank wherein the dynamic damper is located inside of the high voltage tank.

12. A method of protecting against tube-spit in an X-ray generator, the method comprising:
 supplying an X-ray tube with a high voltage potential from a high voltage tank assembly with a transformer;
 interposing a dynamic damper between a cathode of the X-ray tube and the transformer, wherein the dynamic damper provides a frequency variable impedance;
 providing a first impedance of the dynamic damper while supplying the X-ray tube with the high voltage potential; and
 providing a second impedance of the dynamic damper upon occurrence of tube-spit within the X-ray tube, wherein the second impedance is greater than the first impedance.

13. The method of claim 12, further comprising:
 selectively providing a first kV level to the X-ray tube from the high voltage tank assembly; and
 selectively providing a second kV level to the X-ray tube from the high voltage tank assembly;
 wherein the second kV level is greater than the first kV level.

14. The method of claim 13, wherein the high voltage tank assembly further comprises a plurality of switching devices and at least one capacitor arranged in series to the plurality of switching devices, the plurality of switching devices operable to selectively store and release energy from the at least one capacitor, the method further comprising:
 operating the high voltage tank assembly to provide the first kV level to the X-ray tube;
 receiving and storing energy in the at least one capacitor;
 operating the high voltage tank assembly to provide the second kV level to the X-ray tube; and
 discharging the at least one capacitor to facilitate switching from the first kV level to the second kV level.

15. The method of claim 14, further comprising:
 receiving energy through the dynamic damper; and
 storing the received energy in the at least one capacitor.

16. The method of claim 15, wherein at a frequency less than 50 kHz the dynamic damper has an impedance less than 1/3 of a reference impedance needed to protect a voltage rectifier and the transformer in the high voltage tank assembly, tube-spit within the X-ray tube occurs at a frequency greater than 10 MHz, and wherein the impedance of the dynamic damper increases exponentially at a frequency above 50 kHz to an impedance greater than the reference impedance.

17. The method of claim 15, wherein a high voltage cable is arranged between the high voltage tank assembly and the X-ray tube, and wherein when the high voltage tank assembly is operated to provide the second kV level to the X-ray tube, energy is stored in the high voltage cable, and when the high voltage tank assembly is operated to provide the first kV level to the X-ray tube, the high voltage cable is discharged through the dynamic damper to store energy in the at least one capacitor.

18. A high voltage tank assembly in an X-ray generator comprising:
 a transformer assembly configured to receive high frequency input power;
 a voltage rectifier coupled to the transformer assembly and configured to receive an input voltage from the transformer assembly and provide an output voltage to an X-ray tube; and
 a dynamic damper with a frequency dependent impedance interposed between the X-ray tube and the voltage rectifier, wherein the impedance of the dynamic damper increases with an increase in frequency.

19. The high voltage tank assembly of claim 18, further comprising a distributed resonant energy recovery (DRER) circuit comprising:
 at least one capacitor; and
 a plurality of switching devices arranged in series to the at least one capacitor, the switches operable to selectively store energy in the at least one capacitor,
 wherein the voltage rectifier is configured to provide output voltages to the X-ray tube at a first kV level and at a second kV level, the second kV level higher than the first kV level, and when an output voltage is provided to the X-ray tube at the first kV level, energy is received and stored in the at least one capacitor, and when an output voltage is provided to the X-ray tube at the second kV level, energy is discharged from the at least one capacitor to achieve the second kV level.

20. The high voltage tank assembly of claim 18, wherein the voltage rectifier is a full bridge rectifier or a voltage doubler.

\* \* \* \* \*